United States Patent
Kai (10) Patent No.: US 8,131,478 B2
(45) Date of Patent: Mar. 6, 2012

(54) DATA PROCESSING APPARATUS, MEASUREMENT APPARATUS AND DATA COLLECTION METHOD

(75) Inventor: Akinori Kai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1196 days.

(21) Appl. No.: 11/587,346

(22) PCT Filed: Apr. 27, 2005

(86) PCT No.: PCT/JP2005/008012
§ 371 (c)(1),
(2), (4) Date: Oct. 24, 2006

(87) PCT Pub. No.: WO2005/104933
PCT Pub. Date: Nov. 10, 2005

(65) Prior Publication Data
US 2007/0213938 A1    Sep. 13, 2007

(30) Foreign Application Priority Data
Apr. 28, 2004   (JP) .................................. 2004-134199

(51) Int. Cl.
*G06K 7/14* (2006.01)
*G06Q 50/00* (2006.01)
*A61B 5/00* (2006.01)

(52) U.S. Cl. ........................................................ 702/19
(58) Field of Classification Search ........................ None
See application file for complete search history.

(56) References Cited

U.S. PATENT DOCUMENTS

| | | | |
|---|---|---|---|
| 5,772,586 A * | 6/1998 | Heinonen et al. | 600/300 |
| 5,795,301 A * | 8/1998 | Yasukawa et al. | 600/500 |
| 6,909,793 B1 | 6/2005 | Mori et al. | |
| 6,915,954 B2 * | 7/2005 | Knowles et al. | 235/462.01 |
| 2003/0158693 A1 | 8/2003 | Kai | |
| 2004/0153585 A1 | 8/2004 | Kawatahara et al. | |

FOREIGN PATENT DOCUMENTS

| | | |
|---|---|---|
| JP | 7143962 | 6/1995 |
| JP | 2001-134700 | 5/2001 |
| JP | 2002-147081 | 5/2002 |
| JP | 2002-282217 | 10/2002 |
| JP | 2002-291705 | 10/2002 |
| JP | 2002-368907 | 12/2002 |
| JP | 2003-245328 | 9/2003 |

* cited by examiner

*Primary Examiner* — Michael Borin
(74) *Attorney, Agent, or Firm* — Morgan, Lewis & Bockius LLP (57) ABSTRACT

The present invention provides a data processing system and a data collection method by which measurement data can be read in and transmitted easily, without connecting a terminal for transmitting data with various types of measurement apparatuses, and further provides a measurement apparatus to be used for the data processing system and the data collection method. The data processing system at least uses: a measurement apparatus (10) provided with a display screen (13); a terminal (20); and a server (30). The measurement apparatus (10) includes: a measurement portion for obtaining measurement data; a code transforming portion for transforming the measurement data into a bar code, a two-dimensional code (8) or a composite code; and a display portion for displaying the code on the display screen. The terminal (20) includes; an image pickup portion for picking up an image on the display screen (13) that displays the code; an analysis portion for generating measurement data for transmission by analyzing the code that is picked up; and a transmission portion for transmitting, to the server (30), the measurement data for transmission. The server includes a memory portion for storing the transmitted measurement data for transmission.

2 Claims, 8 Drawing Sheets

DATA PROCESSING APPARATUS, MEASUREMENT APPARATUS AND DATA COLLECTION METHOD

TECHNICAL FIELD

The present invention relates to a data processing apparatus, a measurement apparatus and a data collection method.

BACKGROUND ART

Since patients who suffer from diabetes usually are required to know their own blood glucose levels, portable blood glucose measurement apparatuses that can be carried easily has been used recently. Such a portable blood glucose measurement apparatus is provided with a storage medium for storing measurement data. Thus, a doctor can read out the measurement data from the storage medium of the blood glucose measurement apparatus, and can provide appropriate remedies and advice to the patient, based on the thus read-out measurement data.

Moreover, it is a burden for the patient to visit a medical institution often in order to disclose his/her measurement data to the doctor. Thus, a system for enabling the patient to transmit his/her measurement data to a server of the medical institution via the internet has been utilized recently (for example, see Patent documents 1 to 3).

According to this system, a patient can transmit his/her measurement data to the server immediately, by using a communication equipment such as a mobile phone and a personal computer (hereinafter, called a "PC"). Moreover, the doctor can know the condition of the patient by accessing the server that stores the measurement data, by using PC or the like. Furthermore, the patient can receive advice by e-mails or the like from the doctor.

Such a system using the internet can be applied not only to blood glucose measurement apparatuses but also to other apparatuses, and thus it is considered that the application of the system will become widespread in the future. Examples of the other apparatuses include blood pressure measurement apparatuses, heart rate measurement apparatuses, urinary constituent measurement (urinary analysis) apparatuses, electrocardiogram measurement apparatuses, passometers and the like.

Patent document 1: JP 2002-368904 A
Patent document 2: JP 2002-368907 A
Patent document 3: WO 01/088764

DISCLOSURE OF INVENTION

Problem to be Solved by the Invention

However, in order to transmit the measurement data obtained by the measurement apparatus by using the communication equipment, it is required to connect the measurement apparatus with the communication equipment by wire or wireless, and to transmit the measurement data to the communication equipment. Thus, there accordingly is a problem in that the measurement apparatus is required to be provided with an interface that corresponds to the communication equipment to be connected.

Moreover, the measurement data obtained by the measurement apparatus has a special format, and thus is required to be transformed into a transmittable format in order to be transmitted by the communication equipment. Thus, in the case of using a PC as the communication equipment, there is a problem in that a software for transforming the format is required to be developed for each measurement apparatus.

Furthermore, in the case of using a mobile phone as the communication equipment, there is a problem in that, as shown in Patent documents 1 and 2, an adaptor for transforming the format that intervenes between the mobile phone and the measurement apparatus is necessary, and such an adaptor for each measurement apparatus is required to be developed. Moreover, transmission methods for the mobile phones vary depending on the mobile phone companies and the individual products, and such an adaptor is required to be developed also for each mobile phone company and each product.

The object of the present invention is to solve the above-described problems, and to provide a data processing system and a data collection method in which measurement data can be read in and transmitted easily, without connecting a terminal for transmitting data with various types of measurement apparatuses, and further to provide a measurement apparatus to be used for performing the data processing system and the data collection method.

Means for Solving Problem

In order to attain the above-described object, a first data processing system of the present invention at least includes: a measurement apparatus provided with a display screen; a terminal; and a server, wherein the measurement apparatus includes: a measurement portion for obtaining measurement data; a code transforming portion for transforming the measurement data into a bar code, a two-dimensional code or a composite code; and a display portion for displaying the code that is obtained by the transformation on the display screen. The terminal includes; an image pickup portion for picking up an image on the display screen that displays the code; an analysis portion for generating measurement data for transmission by analyzing the code that is picked up; and a transmission portion for transmitting, to the server, the measurement data for transmission, and the server includes a memory portion for storing the received measurement data for transmission.

In order to attain the above-described object, a second data processing system of the present invention at least includes: a measurement apparatus provided with a display screen; a terminal; and a server, wherein the measurement apparatus includes: a measurement portion for obtaining measurement data; a code transforming portion for transforming the measurement data into a bar code, a two-dimensional code or a composite code; and a display portion for displaying the code that is obtained by the transformation on the display screen. The terminal includes; an image pickup portion for picking up an image on the display screen that displays the code; and a transmission portion for transmitting, to the server, image data on the display screen that is obtained by the image pick-up, and the server includes: an analysis portion for generating measurement data to be stored by analyzing the code that is contained in the received image data; and a memory portion for storing the measurement data to be stored.

Moreover, in order to attain the above-described object, a measurement apparatus of the present invention includes: a measurement portion for obtaining measurement data; a code transforming portion for transforming the obtained measurement data into a bar code, a two-dimensional code or a composite code; and a display portion for displaying the code that is obtained by the transformation.

Furthermore, in order to attain the above-described object, a first data collection method of the present invention is a data collection method for collecting, by a server, measurement data that is transmitted from a measurement apparatus via a terminal, wherein the measurement apparatus transforms the measurement data into a bar code, a two-dimensional code or a composite code and allows a display screen to display the transformed code, and the terminal picks up an image on the display screen that displays the code, generates measurement data for transmission by analyzing the code that is picked up, and transmits the measurement data for transmission, the data collection method including at least a step of receiving the measurement data for transmission and storing the received measurement data for transmission, by the server.

Moreover, in order to attain the above-described object, a second data collection method of the present invention is a data collection method for collecting, by a server, measurement data that is transmitted from a measurement apparatus via a terminal, wherein the measurement apparatus transforms the measurement data into a bar code, a two-dimensional code or a composite code and allows a display screen to display the transformed code, and the terminal picks up an image on the display screen that displays the code, and transmits image data on the display screen that is obtained by the image pick-up. The data collection method including at least a step of receiving the image data, generating measurement data to be stored by analyzing the code that is contained in the received image data and storing the generated measurement data to be stored, by the server.

EFFECTS OF THE INVENTION

As mentioned above, according to the present invention, the measurement data is transformed into a bar code, a two-dimensional code or a composite code, and is displayed on the display screen. Moreover, since the terminal for transmitting the data is provided with an image-pickup function, the measurement data is captured into the terminal as the image data, in a state of being transformed into the code. Thus, according to the present invention, the measurement data can be read in and transmitted easily, without connecting the terminal for transmitting the data with various types of the measurement apparatuses.

BRIEF DESCRIPTION OF DRAWINGS

FIG. 2 is a plan view showing an appearance of the measurement apparatus according to Embodiment 1 of the present invention, more specifically.

DESCRIPTION OF THE INVENTION

In the above-described data processing system and the measurement apparatus of the present invention, the code transforming portion may have a configuration to transform the measurement data into a QR code (registered trademark). Also, the measurement portion may have a configuration to obtain a blood glucose level, a blood pressure, a heart rate, the number of steps, a body weight, a body fat percentage or a cholesterol level of a living body, as the measurement data.

Embodiment 1

A measurement apparatus, a data processing system and a data collection method according to Embodiment 1 of the present invention will be described below with reference to FIGS. 1 to 6. Firstly, configurations of the measurement apparatus and the data processing system according to Embodiment 1 will be described with reference to FIGS. 1 to 5.

The data processing system according to Embodiment 1 mainly is provided with the measurement apparatus, a terminal and a server. Herein, in Embodiment 1, an example where the measurement apparatus is a blood glucose measurement apparatus will be described, but the measurement apparatus of Embodiment 1 is not limited to the blood glucose measurement apparatus.

Figure 1:
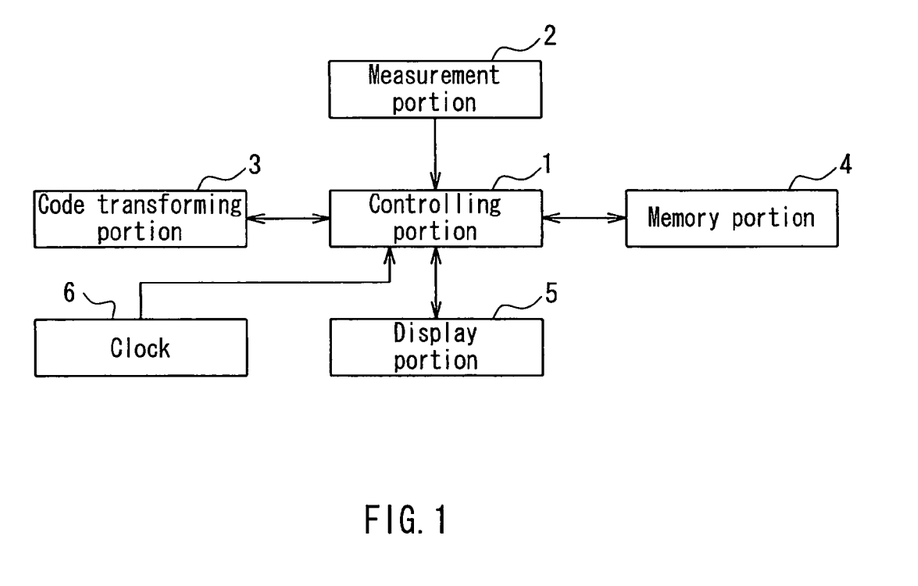
FIG. 1 is a block diagram showing a configuration of a measurement apparatus according to Embodiment 1 of the present invention.

FIG. 1 is a block diagram showing a configuration of the measurement apparatus according to Embodiment 1 of the present invention. As shown in FIG. 1, the measurement apparatus mainly is provided with a controlling portion 1, a measurement portion 2, a code transforming portion 3, a memory portion 4, a display portion 5 and a dock 6. In addition, the measurement apparatus is portable and compact.

The measurement portion 2 obtains measurement data. More specifically, the measurement portion 2 outputs the measurement data for specifying a blood glucose level of a living body to the controlling portion 1, based on information from a sensor (not illustrated) for measuring the blood glucose level of the living body. The measurement data that is output to the controlling portion 1 is output to the memory portion 4 by the controlling portion 1, and is stored in the memory portion 4. Moreover, at this time, the controlling portion 1 also outputs, to the memory portion 4, time information that is output from the dock 6. This time information specifies a measurement date and time, which is stored in the memory portion 4 as a part of the measurement data.

Moreover, in the memory portion 4, adding information to be added to the measurement data is stored in advance. Examples of the adding information include an apparatus ID by which the server (see FIGS. 4 and 5) identifies the measurement apparatus, a user ID for specifying the user who uses the measurement apparatus, a name of a measurement item, management information, a mealtime of the user and the like. Herein, when the user pushes an input button (not illustrated) that is provided on the measurement apparatus at his/her mealtime, the controlling portion 1 outputs the time information at this time to the memory portion 4, whereby the mealtime of the user is obtained.

The code transforming portion 3 transforms the measurement data that is obtained by the measurement portion 2 into a bar code, a two-dimensional code or a composite code. Herein, in Embodiment 1, the controlling portion 1 obtains the measurement data (including the measurement date and time) and the adding information from the memory portion 4, and outputs the measurement data, to which the adding information is added, to the code transforming portion 3. Thus, the code transforming portion 3 transforms the measurement data, to which the adding information is added, into the bar code, the two-dimensional code or the composite code.

Moreover, in Embodiment 1, the code transforming portion 3 can transform the measurement data into either of a bar code, a two-dimensional code and a composite code. Thus, even in the case where the terminal (illustrated in FIGS. 3 and 5) can analyze only any of a bar code, a two-dimensional code and a composite code, the code transforming portion 3 is compatible with the terminal. Herein, the code transforming portion 3 may have a configuration that is capable of transforming the measurement data only into any of a bar code, a two-dimensional code and a composite code.

In Embodiment 1, it is preferable to use the bar code, the two-dimensional code or the composite code that satisfies the international standard. Examples of the bar code include a JAN code, an ITF code, a NW-7 code and the like. Moreover, examples of the two-dimensional code include a QR (Quick Response) code (registered trademark), a data code (ECC200), a ST code (registered trademark) and the like. Examples of the composite code include combinations of the above-described examples of the bar code with the above-described examples of the two-dimensional code. The code formed by the code transforming portion 3 is displayed on the display screen (not illustrated in FIG. 1) of the display portion 5.

Figure 2A:
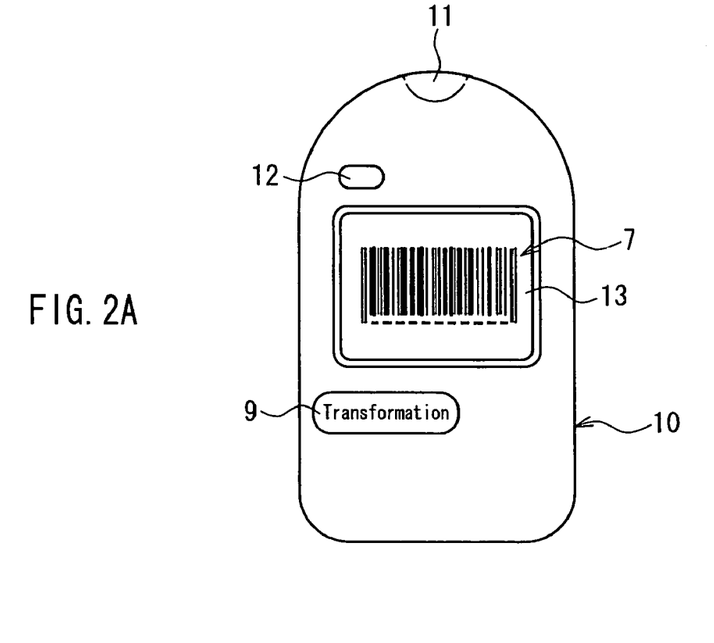
FIG. 2A shows a state where a bar code is displayed on a display screen.
Figure 2B:
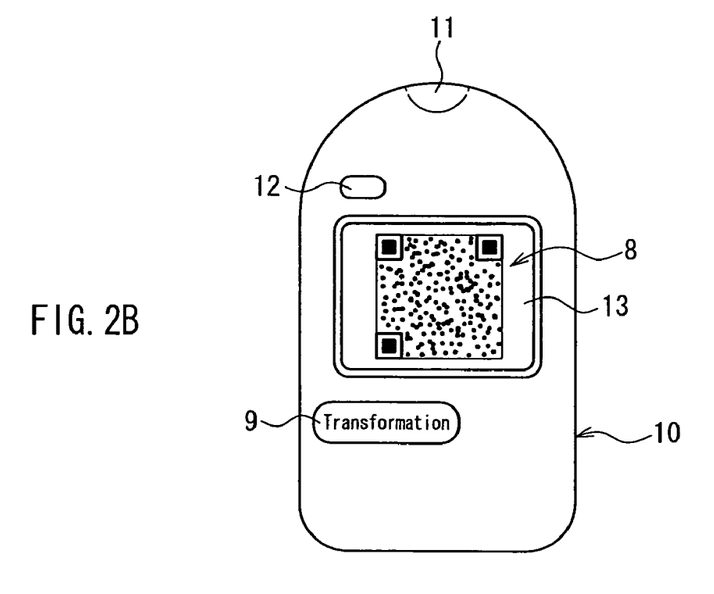
FIG. 2B shows a state where a two-dimensional code is displayed on the display screen.

FIG. 2 is a plan view showing the appearance of the measurement apparatus according to Embodiment 1 of the present invention, more specifically, FIG. 2A shows a state where a bar code is displayed on a display screen, and FIG. 2B shows a state where a two-dimensional code is displayed on the display screen.

A measurement apparatus 10 shown in FIG. 2 is of a palm size, and can be carried by a user. As shown in FIGS. 2A and 2B, on an exterior of the measurement apparatus 10, a code transforming button 9, a sensor mounting portion 11, a power button 12 and a display screen 13 are provided. In addition, an input button by which a user performs various operations with respect to the measurement apparatus 10 further is provided on the measurement apparatus 10, which is not illustrated in FIG. 2.

To the sensor mounting portion 11, a sensor (not illustrated) for measuring a blood glucose level is attached. The user measures his/her blood glucose level by attaching, to this sensor, a very small quantity of his/her blood drawn from his/her fingertip or the like. Moreover, this sensor for measuring a blood glucose level is disposable, and the user attaches a new sensor to the sensor mounting portion 11 every time he/she measures.

After the completion of the measurement, the display screen 13 displays a blood glucose level, a measurement date and time, and the like, in characters and numerals. Thereafter, when the user pushes the code transforming button 9, the display screen 13 displays a bar code 7 shown in FIG. 2A and a QR code (registered trademark) 8 shown in FIG. 2B.

In the example shown in FIGS. 1 and 2, a lightweight and thin display such as a liquid crystal display and an EL display is used as the display portion 5 (see FIG. 1), in order to reduce the size of the measurement apparatus. However, it is necessary to display a bar code and a two-dimensional code on the display screen 13, as shown in FIG. 2. For example, in the case of displaying the QR code (registered trademark), 21×21 cells at the minimum are necessary, and further, at least 29×29 cells are necessary to provide a margin. Thus, it is preferable to use a display having a resolution of 177×177 cells or more, or a resolution of 185×185 cells or more to provide the margin, as the display portion 5 of the measurement apparatus 10. Also, a lightweight and thin display that will be developed in the future can be used as the display portion of the measurement apparatus.

The measurement apparatus shown in FIGS. 1 and 2 is a blood glucose measurement apparatus, but the measurement apparatus of the present invention may be a measurement apparatus other than this. More specifically, examples of the other measurement apparatus include a blood pressure measurement apparatus, a heart rate measurement apparatus, a urinary constituent measurement (urinary analysis) apparatus, an electrocardiogram measurement apparatus, a passometer (pedometer), a body-weight measurement apparatus (scale), a body fat percentage measurement apparatus (body fat monitor), a body temperature measurement apparatus (clinical thermometer), a cholesterol level measurement apparatus (cholesterol monitor) and the like. In this case, the measurement portion 2 obtains a blood pressure, a heart rate, the number of steps, a body weight, a body fat percentage, a cholesterol level or the like of a living body as the measurement data.

Moreover, for example, in the case where the measurement apparatus is a blood pressure measurement apparatus, the measurement portion 2 outputs the measurement data for specifying a blood pressure to the controlling portion 1. Furthermore, in the case where the measurement apparatus is a heart rate measurement apparatus, the measurement portion 2 outputs the measurement data for specifying a heart rate to the controlling portion 1. The parts except the measurement portion 2 can be structured similarly to the example of FIG. 1.

Figure 3:
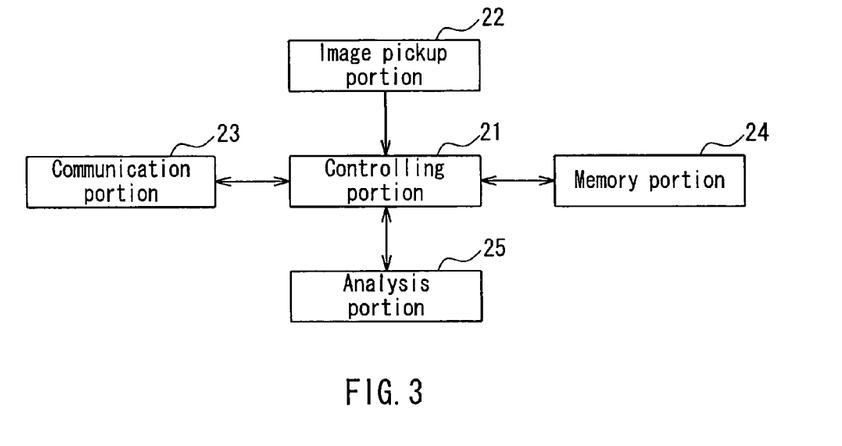
FIG. 3 is a block diagram showing a configuration of a terminal according to Embodiment 1 of the present invention.

FIG. 3 is a block diagram showing a configuration of a terminal according to Embodiment 1 of the present invention. As shown in FIG. 3, the terminal is provided with a controlling portion 21, an image pickup portion 22, a communication portion 23, a memory portion 24 and an analysis portion 25.

The image pickup portion 22 picks up an image on the display screen 13 (see FIG. 2) of the measurement apparatus that displays the bar code, the two-dimensional code or the composite code, and outputs image data to the controlling portion 21. In Embodiment 1, the image pickup portion 22 is constituted of an image pickup lens, an image pickup device such as a CCD and a CMOS, a peripheral circuit for outputting the image data and the like, which are not illustrated in the figure.

The image data that is input into the controlling portion 21 is output from the controlling portion 21 to the memory portion 24, and is stored in the memory portion 24. The analysis portion 25 reads in the image data that is stored in the memory portion 24 via the controlling portion 21, and analyzes the bar code, the two-dimensional code or the composite code that is picked up, thereby generating measurement data for transmission.

Herein, in the case where the image quality of the image data is low, the case where a part of the bar code, the two-dimensional code or the composite code of the image data is lacked or the like, the analysis cannot be performed, and the analysis portion 25 outputs a signal for noting the controlling portion 21 that the analysis cannot be performed. In such a case, the controlling portion 21 can allow a display screen (not illustrated) of the terminal to display a notification of the necessity to perform the photographing again.

Moreover, in Embodiment 1, the analysis portion 25 analyzes the code, by comparing: plural bar patterns or plural cell patterns that are stored in the memory portion 24 in advance as a reference; with a pattern that is specified by the image data. Furthermore, the cell patterns or the bar patterns as the reference are stored in the memory portion 24 so as to correspond to character codes that can be treated by the terminal. Thus, the measurement data that can be transmitted by the terminal is generated due to the analysis by the analysis portion 25.

The measurement data for transmission that is generated by the analysis portion 25 is transmitted to an external server (see FIGS. 4 and 5) by the communication portion 23. The communication portion 23 is structured to be capable of transmitting and receiving data via the internet. Also, the communication portion 23 may be provided with only a function to transmit, to the server, the measurement data for transmission. However, in Embodiment 1, the communication portion 23 is provided also with a function to receive the data. Thus, the terminal also can receive the data from the server.

In Embodiment 1, the terminal can be realized by installing software for analyzing a bar code, a two-dimensional code or a composite code into a mobile phone that is provided with, for example, a CCD camera or a CMOS camera and a function to connect to the internet. In this case, a CPU of the mobile phone functions as the controlling portion 21 and the analysis portion 25 shown in FIG. 3. Also, the function to analyze a bar code, a two-dimensional code or a composite code can be applied by providing a special chip for performing the analysis to the mobile phone.

Also, by connecting an external camera such as a USB camera to a general PC or PDA that can be connected to the internet, and installing the software for analyzing the bar code, the two-dimensional code or the composite code into the PC or the PDA, the terminal according to Embodiment 1 can be realized. In this case, a CPU of the PC or the PDA functions as the controlling portion 21 and the analysis portion 25 shown in FIG. 3.

Figure 4:
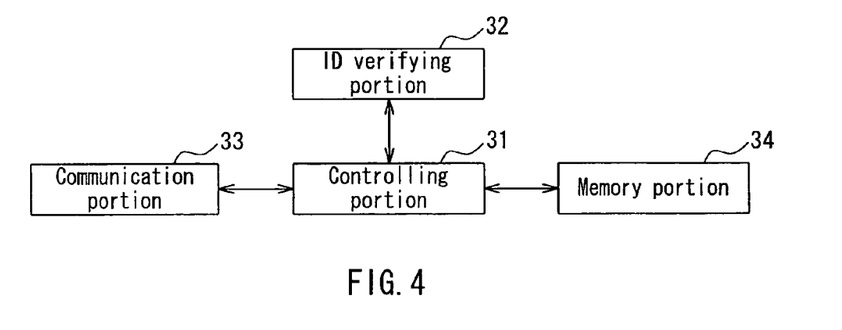
FIG. 4 is a block diagram showing a configuration of a server according to Embodiment 1 of the present invention.

FIG. 4 is a block diagram showing a configuration of the server according to Embodiment 1 of the present invention. As shown in FIG. 4, the server is provided with a controlling portion 31, an ID verifying portion 32, a memory portion 34 and a communication portion 33. The communication portion 33 is structured to be capable of transmitting and receiving data with respect to the terminal shown in FIG. 3 via the internet. The measurement data transmitted from the terminal is received by the communication portion 33, and is output to the controlling portion 31.

The controlling portion 31 extracts an apparatus ID and a user ID from the input measurement data, and outputs them to the ID verifying portion 32. The ID verifying portion 32 judges whether the input apparatus ID and the input user ID respectively are matched with a registered apparatus ID and a registered user ID, and outputs the result to the controlling portion 31. Herein, the registered apparatus ID and the registered user ID are stored in the memory portion 34.

Moreover, in the case where the apparatus ID and the user ID already have been registered, the controlling portion 31 allows the memory portion 34 to store the measurement data. On the other hand, in the case where the apparatus ID and the user ID have not been registered, the controlling portion 31 notifies the terminal that they have not been registered.

Figure 5:
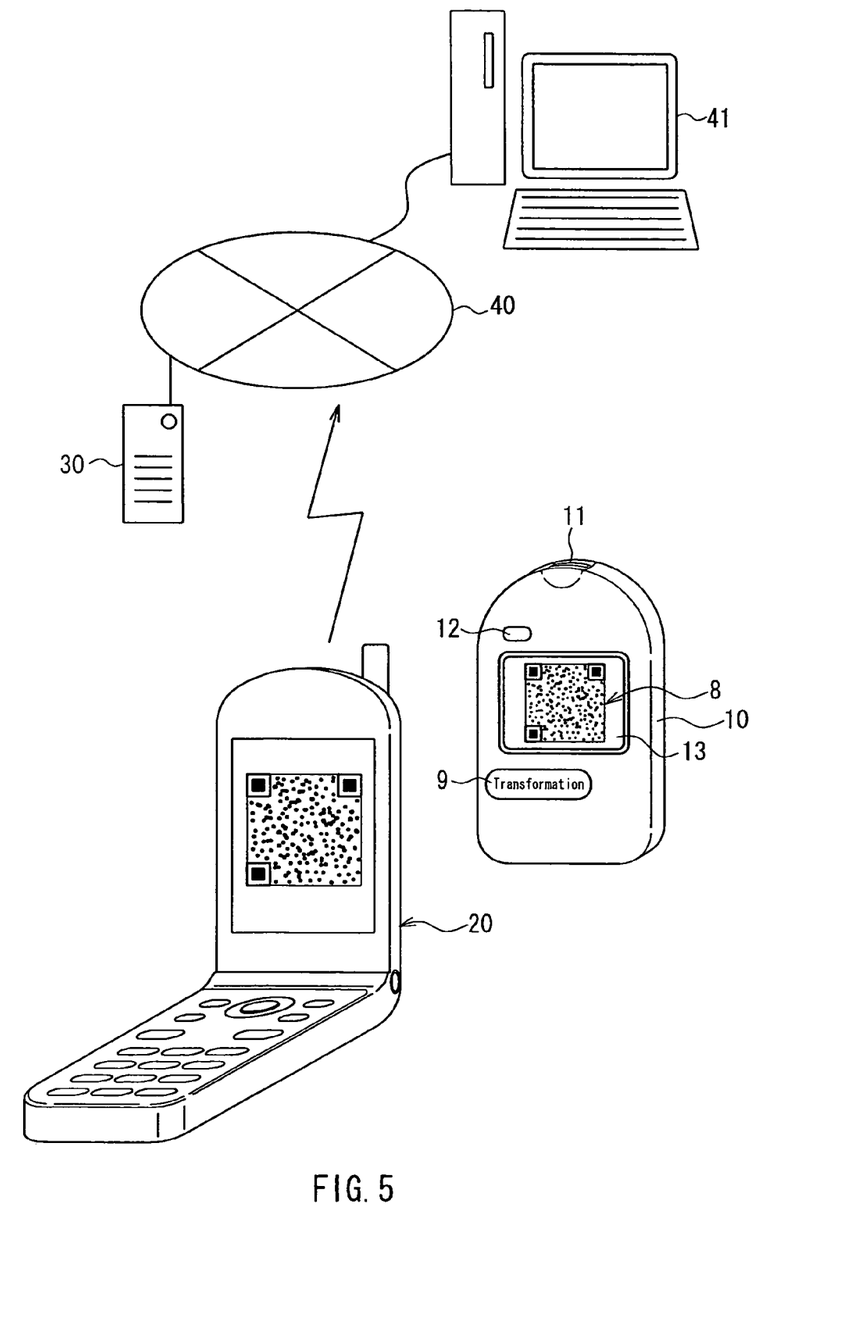
FIG. 5 is a view showing an entire configuration of a data processing system according to Embodiment 1 of the present invention.

Herein, an overall configuration of the data processing system according to Embodiment 1 of the present invention will be described with reference to FIG. 5. In the example of FIG. 5, a mobile phone 20 is used as the terminal. The mobile phone 20 is provided with a function to connect to the internet 40 and display contents of a web-page, and a function to pick up images by using an image pickup device that is provided in the mobile phone 20. Moreover, the mobile phone 20 is provided with software for analyzing the bar code and the two-dimensional code. Furthermore, the measurement apparatus is structured to display the measurement data in the form of the QR code (registered trademark) 8 on the display screen 13.

In the data processing system shown in FIG. 5, a user can photograph the QR code (registered trademark) 8 that is displayed on the display screen 13 of the measurement apparatus 10, by using the mobile phone 20, and further allows the mobile phone 20 to analyze the photographed image so as to form the measurement data for transmission.

Moreover, in the example of FIG. 5, the server 30 is a web server. Thus, the user accesses a web-page of the server 30 by using the mobile phone 20, and transmits the measurement data from the mobile phone 20 to the server 30 via the web-page. Furthermore, the measurement data of the user that is accumulated in the server 30 is displayed on the display screen of the mobile phone 20 via the web-page.

Moreover, a doctor can access the web-page of the server 30 by using a PC 41 that is connected to the internet 40, and can browse the measurement data of the user by a browser of the PC. Furthermore, the doctor can provide advice based on the measurement data to the user by sending e-mails to the mobile phone 20 of the user.

Figure 6:
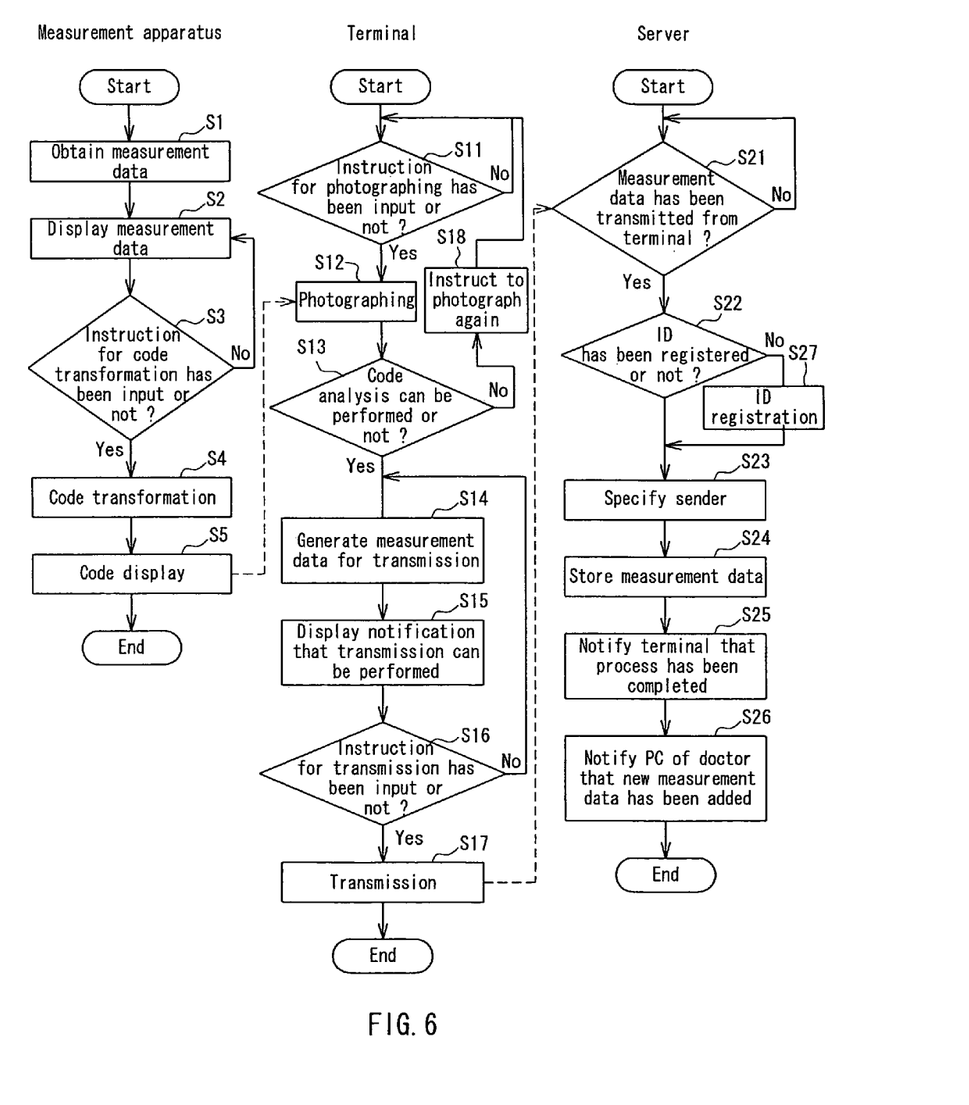
FIG. 6 is a flow chart showing operations of the data processing system according to Embodiment 1 of the present invention.

Next, operations of the data processing system according to Embodiment 1 shown in FIGS. 1 to 5 will be described with reference to FIG. 6. FIG. 6 is a flow chart showing the processes that are performed by the data processing system according to Embodiment 1 of the present invention. In FIG. 6, flows of the respective processes of the measurement apparatus 10, the terminal (mobile phone 20) and the server 30 are shown. Moreover, by operating the data processing system of Embodiment 1, the data collection method of Embodiment 1 is performed by the server 30. In the below description, FIGS. 1 to 5 are referred to as appropriate.

As shown in FIG. 6, in the measurement apparatus 10, the measurement data firstly is obtained by the measurement portion 2 (Step S1). At this time, the controlling portion 1 stores the obtained measurement data together with the time information into the memory portion 4. Subsequently, the obtained measurement data is displayed in numerals on the display screen of the display portion 5 (Step S2). Thereby, the user can check the measurement data.

Next, the controlling portion 1 of the measurement apparatus 10 judges whether the user has input the instruction for the code transformation or not (Step S3). More specifically, the controlling portion 1 judges whether the code transforming button 9 (see FIG. 2) has been pushed or not. In the case of being pushed, the code transforming portion 3 reads out the measurement data, the time information and the adding information from the memory portion 4, and transforms the measurement data, to which the adding information and the time information are added, into a bar code, a two-dimensional code or a composite code (Step S4).

Thereafter, the bar code, the two-dimensional code or the composite code that is obtained in Step S4 is displayed on the display screen 13 of the measurement apparatus 10 (Step S5), and the processes of the measurement apparatus 10 are completed.

Also, in Embodiment 1, after obtaining the measurement data in Step S1 and displaying the measurement data in Step S2 plural times, the judgment in Step S3 and the transformation in Step S4 may be performed. In this case, Steps S3 to S5 are performed plural times for each set of the obtained measurement data.

Moreover, as shown in FIG. 6, in the mobile phone 20, the controlling portion 21 firstly judges whether the instruction for photographing has been input by the user or not, that is, the shutter button has been pushed or not (Step S11). Herein, the image that is picked up by the image pickup portion 22 is displayed on the display screen of the mobile phone 20 in real time, until the shutter button is pushed.

In the case where the shutter button has been pushed, the controlling portion 21 allows the image pickup portion 22 to perform photographing (Step S12). More specifically, the controlling portion 21 allows the image pickup portion 22 to perform an electronic shutter operation and to output the image data.

Next, after the controlling portion 21 outputs the image data to the analysis portion 25, the analysis portion 25 judges whether the bar code, the two-dimensional code or the composite code that is contained in the image data can be analyzed or not (Step S13).

In the case where image quality of the image data is low, the case where a part of the code contained in the image data is lacked or the like, the analysis portion 25 judges that the analysis cannot be performed, and notifies the controlling portion 21 that the analysis cannot be performed. In this case, the controlling portion 21 allows the display screen of the mobile phone 20 to display a notification that the photographing will be performed again (Step S18). On the other hand, in the case where the analysis portion 25 judges that the analysis can be performed, the analysis portion 25 generates the measurement data for transmission (Step S14). Furthermore, the controlling portion 21 allows the display screen to display a notification that the transmission can be performed (Step S15).

Subsequently, the controlling portion 21 judges whether an instruction for the transmission has been input by the user or not (Step S16), and in the case where the instruction has been input, the controlling portion 21 transmits, to the server 30, the measurement data for transmission (Step S17). Thereby, the processes of the mobile phone 20 are completed. As mentioned above, in the case where the plural sets of the measurement data are obtained by the measurement apparatus 10, Steps S11 to S17 are performed for each set of the obtained measurement data.

Moreover, in Embodiment 1, as mentioned above, since the server is the web-server, the user accesses the web-page by using the terminal, and transmits the data on the web-page. Furthermore, in the case where the terminal is a mobile phone, a PC or the like, the measurement data can be transmitted easily by registering a URL of the web-page of the server. Moreover, in the case where the transmission of the measurement data is not completed normally, the server 30 notifies that the transmission of the measurement data is not completed normally, and the notification is displayed on the web-page, which is not illustrated in the figure.

Moreover, as shown in FIG. 6, the server 30 firstly judges whether the measurement data has been transmitted from the mobile phone 20 or not (Step S21). In the case where the measurement data has not been transmitted yet, the server 30 assumes in a standby state. Furthermore, even in the case where the measurement data has been transmitted but the transmission has not been completed normally, the notification that the transmission has not been completed normally is displayed on the web-page, and the server 30 assumes in a standby state, as mentioned above.

In the case where the measurement data has been transmitted and the transmission has been completed normally, the ID verifying portion 32 judges whether the apparatus ID and the user ID contained in the measurement data already have been registered or not (Step S22).

In the case where the apparatus ID and the user ID already have been registered, the controlling portion 31 of the server 30 specifies the sender (the measurement apparatus and the user) by the apparatus ID and the user ID (Step S23), and allows the memory portion 34 to store the measurement data (Step S24). In the memory portion 34, the measurement data is accumulated for each of the users.

On the other hand, in the case where the apparatus ID and the user ID have not been registered yet, the controlling portion 31 of the server 30 shows, on the web-page, the notification that these IDs have not been registered yet. Moreover, a registration page for the user's ID registration is shown so as to let the user to register his/her ID (Step S27). When the user registers his/her ID, the process proceeds to Step S23.

Next, the controlling portion 31 notifies the mobile phone 20 the completion of the process via the communication portion 33 (Step S25). In Embodiment 1, the web-page shows the notification that the process for storing the measurement data has been completed. Subsequently, the controlling portion 31 notifies the PC 41 of the registered doctor that the new measurement data has been added (Step S26). In Embodiment 1, the notification is transmitted to the PC 41 of the doctor by an e-mail. As mentioned above, the processes of the server 30 are completed.

In addition, in the case where the plural sets of the measurement data are obtained by the measurement apparatus 10, and Steps S11 to S17 are performed for each set of the obtained measurement data, as described above, Steps S21 to S26 also are performed for each set of the obtained measurement data.

As described above, according to Embodiment 1, the measurement data that is obtained by the measurement apparatus can be captured into the terminal so as to be transmitted, without connecting the measurement apparatus with the terminal via an adaptor or a cable. Therefore, no interface for the connection is required to be provided in the measurement apparatus, unlike the conventional measurement apparatus, thereby reducing the cost for manufacturing the measurement apparatus.

Moreover, according to Embodiment 1, since the measurement data is transformed into the bar code, the two-dimensional code or the composite code, the terminal (the mobile phone 20 or the like) that is provided with the analyzing function can capture the measurement data from any type of the measurement apparatus, and can transmit the measurement data. Thus, it is not necessary to develop software for each measurement apparatus, unlike the conventional one.

Moreover, since the bar code, the two-dimensional code or the composite code that satisfies the international standard can be used, the development of the software for analyzing the bar code, the two-dimensional code or the composite code is quite easy. Therefore, various types of mobile phones with different transmission methods can be used as the terminal.

Embodiment 2

Next, a measurement apparatus, a data processing system and a data collection method according to Embodiment 2 of the present invention will be described with reference to FIGS. 7 to 9. Firstly, configurations of the measurement apparatus and the data processing system according to Embodiment 2 will be described with reference to FIGS. 7 and 8.

The data processing system according to Embodiment 2 mainly is provided with a measurement apparatus, a terminal and a server, similarly to the data processing system of Embodiment 1. The measurement apparatus according to Embodiment 2 is similar to the measurement apparatus according to Embodiment 1 shown in FIGS. 1 and 2. Moreover, also in Embodiment 2, the measurement apparatus is a blood glucose measurement apparatus. Herein, similarly to Embodiment 1, the measurement apparatus is not limited to the blood glucose measurement apparatus.

Figure 7:
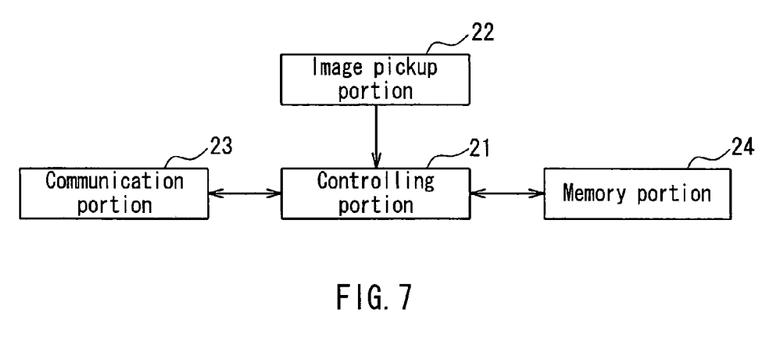
FIG. 7 is a block diagram showing a configuration of a terminal according to Embodiment 2 of the present invention.

FIG. 7 is a block diagram showing a configuration of a terminal according to Embodiment 2 of the present invention. As shown in FIG. 7, in Embodiment 2, the terminal is not provided with an analysis portion for the code analyses, which is distinct from the terminal according to Embodiment 1 in this point. Thus, the terminal according to Embodiment 2 transmits an image data of an image that is picked up by the image pickup portion 22 to the server.

Moreover, also in Embodiment 2, a mobile phone, a PC and a PDA can be used as the terminal. However, in Embodiment 2, the terminal is not required to be provided with the analyzing function to analyze a bar code, a two-dimensional code or a composite code. Thus, a terminal that is provided with a CCD camera or a CMOS camera and a function to transmit the image data can be used as the terminal according to Embodiment 2.

Figure 8:
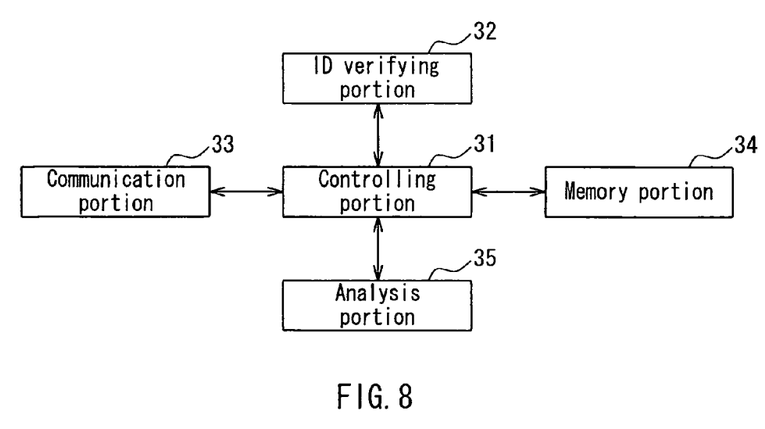
FIG. 8 is a block diagram showing a configuration of a server according to Embodiment 2 of the present invention.

FIG. 8 is a block diagram showing a configuration of the server according to Embodiment 2 of the present invention. As shown in FIG. 8, the server according to Embodiment 2 is provided with an analysis portion 35, unlike the server according to Embodiment 1. Thus, in Embodiment 2, a bar code, a two-dimensional code or a composite code is analyzed in the server. Except for this point, the configuration of the server according to Embodiment 2 is similar to that of Embodiment 1, and also is provided with the controlling portion 31, the ID verifying portion 32, the memory portion 34 and the communication portion 33. Moreover, also in Embodiment 2, the server is a web-server, similarly to that of Embodiment 1.

The analysis portion 35 of the server has a function that is similar to the function of the analysis portion 25 of the terminal according to Embodiment 1 shown in FIG. 3. More specifically, the code analysis also is performed by the analysis portion 35, by comparing: plural bar patterns or plural cell patterns that are stored in the memory portion 34 of the server in advance as a reference; with a pattern that is specified by the image data transmitted from the terminal. Moreover, the cell patterns or the bar patterns as the reference are stored so as to correspond to character codes that can be treated by the server. Therefore, due to the analysis by the analysis portion 35 of the server, measurement data that can be stored in the server is generated.

Moreover, in Embodiment 2, in the case where image quality of the image data is low, the case where a part of the bar code, the two-dimensional code or the composite code of the image data is lacking or the like, the server notifies the terminal that the analysis cannot be performed.

Next, operations of the data processing system according to Embodiment 2 will be described with reference to FIG. 9. FIG. 9 is a flow chart showing processes that are performed by the data processing system according to Embodiment 2 of the present invention. Also in FIG. 9, flows of the respective processes of the measurement apparatus, the terminal and the server are shown, similarly to FIG. 6. Herein, by operating the data processing system according to Embodiment 2, the data collection method according to Embodiment 2 is achieved by the server. In the below description, FIGS. 7 and 8 are referred to as appropriate.

Figure 9:
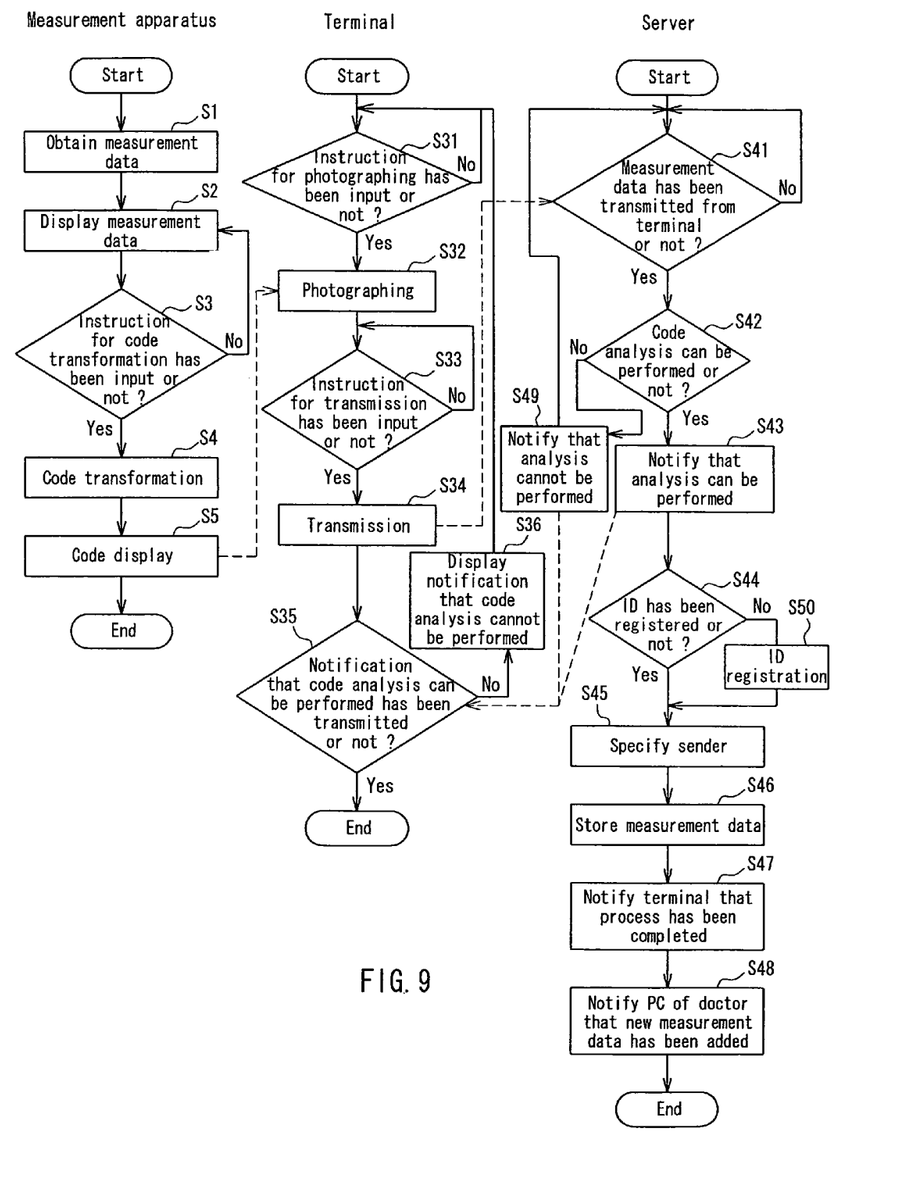
FIG. 9 is a flow chart showing processes that are performed by a data processing system according to Embodiment 2 of the present invention.

As shown in FIG. 9, in the measurement apparatus, the processes that are similar to the processes of Embodiment 1 shown in FIG. 6 are performed. That is, by performing Steps S1 to S5, the bar code, the two-dimensional code or the composite code is displayed on the display screen of the measurement apparatus.

Moreover, as shown in FIG. 9, in the terminal (for example, a mobile phone), the controlling portion 21 firstly judges whether an instruction for photographing has been input by the user or not (Step S31). Step S31 is a step that is similar to Step 11 shown in FIG. 6. Also in Embodiment 2, the image that is picked up by the image pickup portion 22 is displayed on the display screen of the terminal in real time, until the shutter button is pushed.

In the case where the shutter button is pushed, the controlling portion 21 allows the image pickup portion 22 to perform photographing (Step S32). Step S32 is a step that is similar to Step S12 shown in FIG. 6. Subsequently, the controlling portion 21 judges whether an instruction for the transmission has been input by the user or not (Step S33), and in the case where the instruction has been input, the controlling portion 21 transmits the image data obtained in Step S32 to the server (Step S34).

Herein, also in Embodiment 2, the server is a web-server, as described above. Thus, the user accesses the web-page by using the terminal, and transmits the data on the web-page.

Moreover, in Embodiment 2, the server notifies the controlling portion 21 whether the code analysis can be performed or not, as described above. Thus, after the completion of Step S34, the controlling portion 21 checks whether the notification that the code analysis can be performed has been transmitted from the server or not (Step S35).

In the case where, instead of the notification that the code analysis can be performed, a notification that the code analysis cannot be performed has been transmitted, the display screen (not illustrated) of the terminal displays the notification that the code analysis cannot be performed (Step S36). On the other hand, in the case where the notification that the code analysis can be performed is transmitted, the processes of the terminal are completed. Herein, as described above, since the server is the web-server, the notification whether the code analysis can be performed or not is shown on the web-page that is displayed on the display screen of the terminal.

Moreover, as shown in FIG. 9, the server firstly judges whether the measurement data has been transmitted from the terminal or not (Step S41). Step S41 is a step that is similar to Step 21 shown in FIG. 6. In the case where the measurement data has not been transmitted yet, the server assumes in a standby state. Furthermore, also in Embodiment 2, in the case where the transmission of the measurement data has not been completed normally, the notification that the transmission has not been completed normally is shown on the web-page, and the server assumes in a standby state.

In the case where the measurement data has been transmitted from the terminal, the analysis portion 35 of the server judges whether the code analysis can be performed or not (Step S42). In the case where the image quality of the image data is low, the case where a part of the code contained in the image data is lacked or the like, the analysis portion 35 notifies the controlling portion 31 that the code analysis cannot be performed. Thus, the controlling portion 31 notifies the terminal that the code analysis cannot be performed, via the communication portion 33 (Step S49).

On the other hand, in the case where the code analysis can be performed, the controlling portion 31 notifies the terminal that the code analysis can be performed, via the communication portion 33 (Step S43). In Embodiment 2, these notifications are shown on the web-page of the server.

When the notification that the code analysis can be performed is transmitted to the terminal, the ID verifying portion 32 judges whether the apparatus ID and the user ID contained in the measurement data have been already registered or not (Step S44). Step S44 is a step that is similar to Step S22 shown in FIG. 6.

In the case where the apparatus ID and the user ID have been registered, the controlling portion 31 of the server specifies the sender (the measurement apparatus and the user) by the apparatus ID and the user ID (Step S45), and allows the memory portion 34 to store the measurement data (Step S46). Steps S45 and S46 are steps that are similar to Steps S23 and S24 shown in FIG. 6, respectively.

On the other hand, in the case where the apparatus ID and the user ID have not been registered, the controlling portion 31 of the server 30 allows the web-page to show the notification that these IDs have not registered. Moreover, a registration page for the user's ID registration is displayed so as to let the user to register his/her ID (Step S50). Step S50 is a step that is similar to Step S27 shown in FIG. 6. When the user registers his/her ID, the process proceeds to Step S45.

Thereafter, the controlling portion 31 notifies the terminal that the process is completed (Step S47), and further sends an e-mail to the PC 41 of the doctor so as to notify that the new measurement data is added (Step S48). Steps S47 and S48 are steps that are similar to Steps S25 and S26 shown in FIG. 6, respectively. Thereby, the processes of the server 30 are completed.

As described above, also in Embodiment 2, the data that is obtained by the measurement apparatus can be captured into the terminal and can be transmitted, without connecting the measurement apparatus with the terminal via an adaptor or a cable, similarly to Embodiment 1. Moreover, similarly to Embodiment 1, the measurement data can be captured into any type of the measurement apparatus, and thus, it is not necessary to develop software for each measurement apparatus, unlike the conventional one.

Moreover, in Embodiment 2, since the analysis of the bar code, the two-dimensional code or the composite code is performed by the server, the terminal is only required to be provided with an image-pickup function and a function to transmit the image data. Therefore, for example, even a mobile phone that cannot be provided with application software can be used as the terminal, and thus the alternatives for the terminal can be wider than those of Embodiment 1.

Embodiment 3

Figure 10:
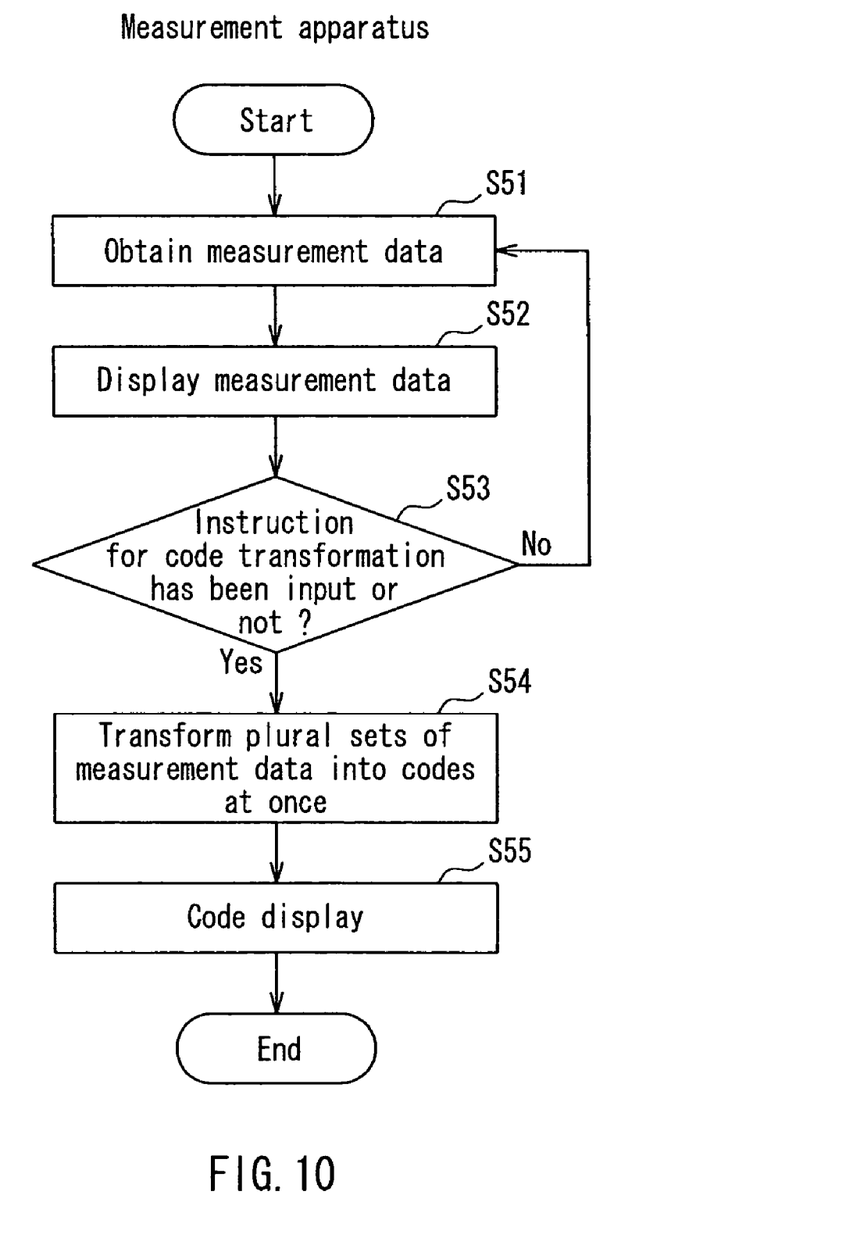
FIG. 10 is a flow chart showing processes that are performed by a measurement apparatus according to Embodiment 3 of the present invention.

Next, a measurement apparatus, a data processing system and a data collection method according to Embodiment 3 of the present invention will be described with reference to FIG. 10. Firstly, configurations of the measurement apparatus and the data processing system according to Embodiment 3 will be described.

Also in Embodiment 3, the data processing system mainly is provided with a measurement apparatus, a terminal and a server. Moreover, the measurement apparatus is a blood glucose measurement apparatus that mainly is provided with a controlling portion, a measurement portion, a code transforming portion, a memory portion, a display portion and a clock, similarly to the measurement apparatus shown in FIG. 1 in Embodiment 1. Furthermore, the measurement apparatus has functions that are similar to those of the measurement apparatus shown in FIG. 1 in Embodiment 1.

However, in Embodiment 3, the measurement apparatus can obtain plural sets of the measurement data, and also can transform the codes of these plural sets of the measurement data at once. More specifically, the controlling portion allows the memory portion to store the plural sets of the measurement data that are output from the measurement portion, together with time information for specifying measurement dates and times of the respective sets of the measurement data. The code transforming portion obtains the plural sets of the measurement data (containing the measurement dates and times) and adding information from the memory portion, and transforms whole information containing all of the information into a bar code, a two-dimensional code or a composite code.

Herein, in Embodiment 3, as the terminal, the terminal shown in FIGS. 3 and 5 in Embodiment 1 or the terminal shown in FIG. 7 in Embodiment 2 can be used. Moreover, as the server, the server shown in FIG. 4 in Embodiment 1 or the server shown in FIG. 8 in Embodiment 2 can be used. Furthermore, also in Embodiment 3, the measurement apparatus is not limited to the blood glucose measurement apparatus.

Next, operations of the data processing system according to Embodiment 3 will be described. In Embodiment 3, processes of the measurement apparatus are different from those of Embodiments 1 and 2. Processes of the terminal and the server are performed similarly to those of Embodiment 1 or 2. Also in Embodiment 3, by operating the data processing system, the server achieves the data collection method according to Embodiment 3.

The processes of the measurement apparatus according to Embodiment 3 will be described with reference to FIG. 10. FIG. 10 is a flow chart showing the processes that are performed by the measurement apparatus according to Embodiment 3 of the present invention. As shown in FIG. 10, the measurement portion 2 of the measurement apparatus firstly obtains the measurement data (Step S51). At this time, the controlling portion allows the memory portion to store the obtained measurement data together with the time information. Subsequently, the obtained measurement data is displayed in numerals on the display screen of the display portion 5 (Step S52). Steps S51 and S52 are steps that are similar to Steps S1 and S2 shown in FIG. 6 in Embodiment 1.

Subsequently, the controlling portion of the measurement apparatus judges whether an instruction for the code transformation has been input by the user or not (Step S53). Step S53 is a step that is similar to Step S3 shown in FIG. 6 in Embodiment 1. Also in Embodiment 3, the controlling portion judges whether the code transforming button (see FIG. 2) has been pushed or not.

In the case where, as a result of the judgment, it is revealed that the instruction for the code transformation has not been input by the user, the measurement apparatus is in a standby state until the next measurement data is obtained. In Embodiment 3, Steps S1 and S2 are repeated, until the number, which is intended by the user, of sets of the measurement data are obtained.

On the other hand, in the case where the instruction for the code transformation has been input by the user, the code transforming portion 3 reads out the plural sets of the measurement data, and the time information and the adding information of the respective sets of the measurement data from the memory portion 4. Moreover, the code transforming portion transforms the plural sets of the measurement data, to which the adding information and the time information are added, into a bar code, a two-dimensional code or a composite code at once (Step S54).

Thereafter, the bar code, the two-dimensional code or the composite code that is obtained in Step S54 is displayed on the display screen of the measurement apparatus (Step S55), and the processes of the measurement apparatus according to Embodiment 3 are completed. Step S55 is a step that is similar to Step S5 shown in FIG. 6 in Embodiment 1.

Thereafter, the terminal and the server perform the processes shown in FIG. 6 in Embodiment 1 or the processes shown in FIG. 9 in Embodiment 2. Herein, in Embodiment 3, since the information containing the plural sets of the measurement data is transmitted to the server, the server allows the memory portion to store the measurement data and its corresponding time information so that they may be linked with each other. Moreover, the server can transfer all of the added plural sets of the measurement data to the PC of the doctor.

As mentioned above, according to Embodiment 3, the plural sets of the measurement data can be transmitted to the server at once. Thus, in the case where the user may transmit, at once, plural sets of the measurement data that are measured in one day, depending on, for example, the condition of the sickness or the like of the user, the user's effort can be reduced. Moreover, the convenience for the user can be increased, also because, in the case where the user is outside a communicative area of the terminal for a certain period of time, the user can transmit untransmitted sets of the measurement data, which are obtained while he/she is outside the communicative area, at once when the he/she returns to the inside of the communicative area of the terminal.

Moreover, also in Embodiment 3, the data that is obtained by the measurement apparatus can be captured into the terminal and can be transmitted, without connecting the measurement apparatus with the terminal via an adaptor or a cable, similarly to Embodiment 1. Furthermore, similarly to Embodiment 1, the measurement data can be captured into any type of the measurement apparatus, and thus, it is not necessary to develop software for each measurement apparatus, unlike the conventional one.

INDUSTRIAL APPLICABILITY

As described above, according to the present invention, measurement data can be read in and transmitted easily, without connecting a terminal for transmitting the data with various types of measurement apparatuses. Therefore, the measurement data that is obtained by the various types of the measurement apparatuses can be processed easily, and the cost for constructing the system can be reduced.

The invention claimed is:

1. A data processing system at least comprising: a portable measurement apparatus provided with a display screen; a terminal; and a server,
wherein the portable measurement apparatus comprises: a measurement portion for obtaining measurement data; a code transforming portion for transforming the measurement data into a bar code, a two-dimensional code or a composite code; a display portion for displaying the code that is obtained by the transformation on the display screen; and a memory portion for storing the measurement data, and the code transforming portion transforms the plural sets of the measurement data, which are stored in the memory portion, into a bar code, a two-dimensional code or composite code at once,
the terminal comprises; an image pickup portion for picking up an image on the display screen that displays the code; an analysis portion for generating measurement data for transmission by analyzing the code that is picked up; and a transmission portion for transmitting, to the server, the measurement data for transmission, and the server comprises a memory portion for storing the received measurement data for transmission.

2. The data processing system according to claim 1, wherein the measurement portion of the measurement apparatus obtains a blood glucose level, a blood pressure, a heart rate, the number of steps, a body weight, a body fat percentage or a cholesterol level of a living body, as the measurement data.

* * * * *